(12) United States Patent (10) Patent No.: US 12,636,035 B2

Murray et al. (45) Date of Patent: May 26, 2026

(54) TISSUE-REMOVING CATHETHER WITH FLEXIBLE DISTAL TIP

(71) Applicant: Medtronic Vascular, Inc., Santa Rosa, CA (US)

(72) Inventors: Aran Murray, Galway (IE); Eoin J. Walsh, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 58 days.

(21) Appl. No.: 18/711,825

(22) PCT Filed: Nov. 18, 2022

(86) PCT No.: PCT/IB2022/061162

§ 371 (c)(1),
(2) Date: May 20, 2024

(87) PCT Pub. No.: WO2023/089567

PCT Pub. Date: May 25, 2023

(65) Prior Publication Data

US 2025/0009380 A1 Jan. 9, 2025

Related U.S. Application Data

(60) Provisional application No. 63/264,270, filed on Nov. 18, 2021.

(51) Int. Cl.
A61B 17/3207 (2006.01)
A61B 17/00 (2006.01)

(52) U.S. Cl.
CPC ................. A61B 17/320758 (2013.01); *A61B 2017/00836* (2013.01); *A61B 2017/00845* (2013.01); *A61B 2017/00862* (2013.01)

(58) Field of Classification Search
None
See application file for complete search history.

(56) References Cited

U.S. PATENT DOCUMENTS

| 5,360,432 | A | | 11/1994 | Shturman et al. |
| 5,632,754 | A | * | 5/1997 | Farley ................ A61B 17/3207 |
| | | | | 606/159 |

(Continued)

FOREIGN PATENT DOCUMENTS

| CA | 2720761 A1 | 10/2009 |

OTHER PUBLICATIONS

International Search Report and Written Opinion for PCT/IB2022/061162, 11 pages, Mar. 13, 2023, Rijswijk, Netherlands.

*Primary Examiner* — Shaun L David
(74) *Attorney, Agent, or Firm* — Stinson LLP

(57) ABSTRACT

The present disclosure provides a tissue-removing catheter for removing tissue in a body lumen including an elongate drive member, tissue-removing element, and a distal tip. The elongate drive member is sized and shaped to be received in the body lumen. The elongate drive member rotates about an axis. The tissue-removing element is operatively coupled to a distal end portion of the elongate drive member and rotates by the elongate drive member to remove tissue in the body lumen. The distal tip extends distally outward from the tissue-removing element and is more flexible than tissue-removing element. The distal tip has a proximal end portion coupled to the tissue-removing element and a distal end portion spaced distally from the tissue-removing element. The distal tip defines a tip in communication with a liner passage that is configured to receive a guidewire therein.

17 Claims, 8 Drawing Sheets

(56)            References Cited

U.S. PATENT DOCUMENTS

| | | | | |
|---|---|---|---|---|
| 6,015,420 | A | * | 1/2000 | Wulfman ....... A61B 17/320758 |
| | | | | 606/108 |
| 2006/0074442 | A1 | | 4/2006 | Noriega et al. |
| 2018/0317952 | A1 | * | 11/2018 | Jamous .......... A61B 17/320783 |
| 2021/0275209 | A1 | | 9/2021 | Jamous et al. |

* cited by examiner

TISSUE-REMOVING CATHETHER WITH FLEXIBLE DISTAL TIP

FIELD

The present disclosure generally relates to a tissue-removing catheter, and more particular, to a tissue-removing catheter including a flexible distal tip.

BACKGROUND

Tissue-removing catheters are used to remove unwanted tissue in body lumens. As an example, atherectomy catheters are used to remove material from a blood vessel to open the blood vessel and improve blood flow through the vessel. This process can be used to prepare lesions within a patient's coronary artery to facilitate percutaneous coronary angioplasty (PTCA) or stent delivery in patients with severely calcified coronary artery lesions. Atherectomy catheters typically employ a rotating element which is used to abrade or otherwise break up the unwanted tissue.

SUMMARY

In one aspect, a tissue-removing catheter for removing tissue in a body lumen generally includes an elongate drive member, tissue-removing element, and a distal tip. The elongate drive member, of the present disclosure, is sized and shaped to be received in the body lumen. Further, the elongate drive member may rotate about a longitudinal axis. The tissue-removing element is operatively coupled to a distal end portion of the elongate drive member. The tissue-removing element rotates by rotation of the elongate drive member to remove tissue in the body lumen. The distal tip extends distally outward from the tissue-removing element and is more flexible than tissue-removing element. The distal tip has a proximal end portion coupled to the tissue-removing element and a distal end portion spaced distally from the tissue-removing element. The distal tip defines a tip opening that extends through the proximal and distal end portions of the distal tip, such that the tip opening is in communication with a liner passage and is configured to receive a guidewire therein.

BRIEF DESCRIPTION OF THE DRAWINGS

Corresponding reference characters indicate corresponding parts throughout the drawings.

DETAILED DESCRIPTION

Figure 1:
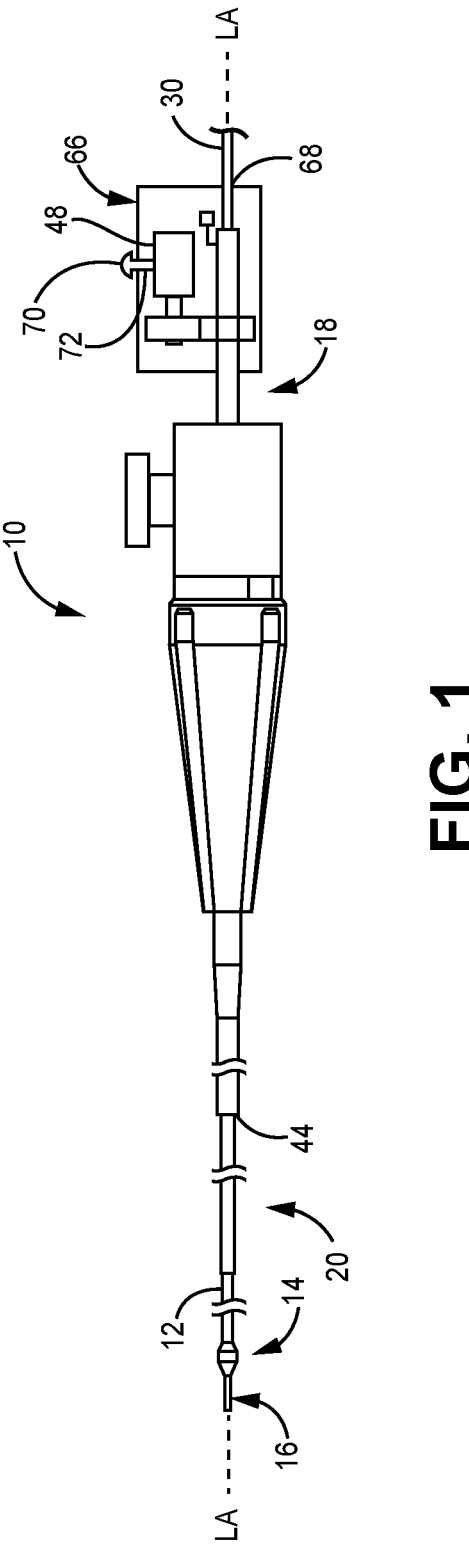
FIG. 1 is a schematic illustration of a catheter of the present disclosure.
Figure 2:
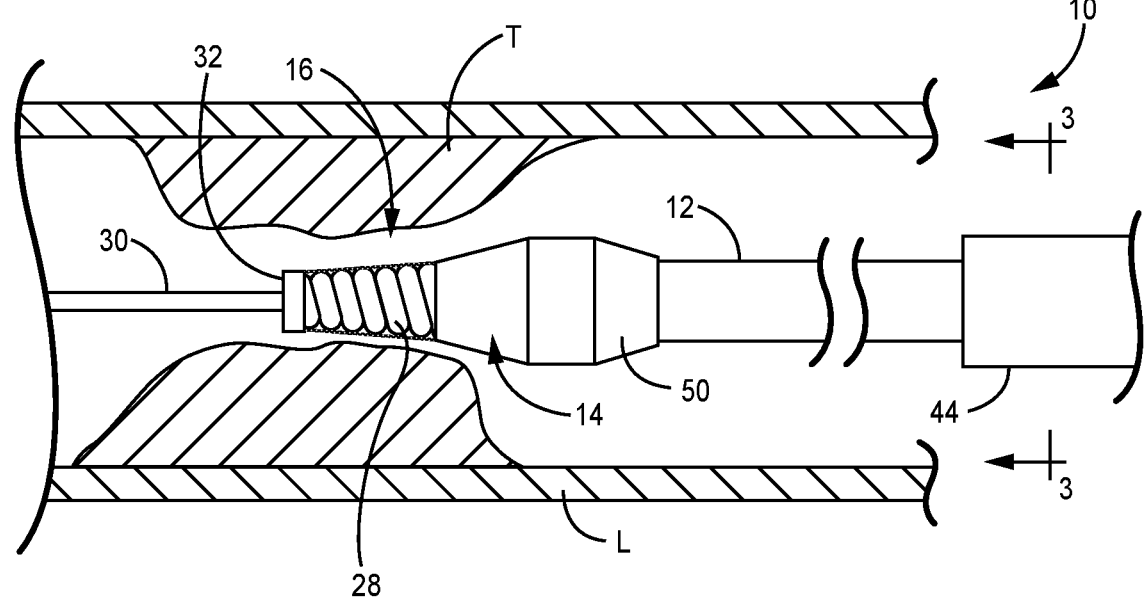
FIG. 2 is an enlarged elevation of an embodiment of a distal end portion of the catheter.

Referring to the drawings, and in particular FIGS. 1-2, a tissue-removing catheter for removing tissue T in a body lumen L is generally indicated at reference number 10. The illustrated catheter 10 is a rotational atherectomy device suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty (PTCA) or the subsequent delivery of a stent. Features of the disclosed embodiments may also be suitable for treating chronic total occlusion (CTO) of blood vessels, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The catheter 10 is sized for being received in the body lumen L (FIG. 2), such as a blood vessel, of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Figure 3:
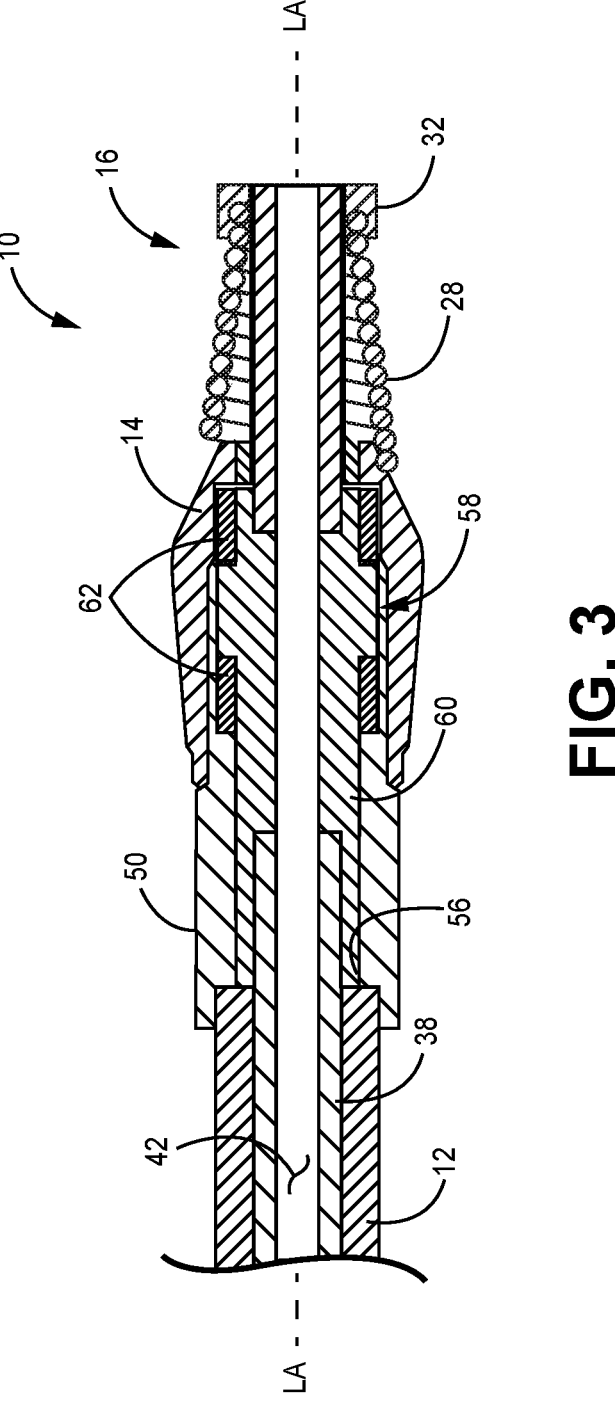
FIG. 3 is an enlarged fragmentary longitudinal cross section of the distal end portion of the catheter in FIG. 2.

Referring to the drawings, and in particular FIGS. 1-2, the tissue-removing catheter 10 for removing tissue T in a body lumen L generally includes an elongate drive member 12, a tissue-removing element 14, and a flexible distal tip 16. As explained in further detail below, the elongate drive member 12 is sized and shaped to be received in the body lumen L. As shown best in FIG. 1, the elongate drive member 12 includes proximal and distal end portions 18, 20 and a longitudinal axis LA extending between the proximal and distal end portions. The proximal and distal end portions 18, 20 are spaced apart from one another along the longitudinal axis LA. Further, the elongate drive member 12 is configured to be rotated about the longitudinal axis LA in accordance with one embodiment. As explained in further detail below, the tissue-removing element 14 is operatively coupled to the distal end portion 20 of the elongate drive member 12. The tissue-removing element 14 rotates by the elongate drive member 12 to remove tissue T (e.g., plaque) in the body lumen L. The flexible distal tip 16 is coupled to (e.g., directly coupled to) and extends distally outward from the tissue-removing element 14. The distal tip 16 is more flexible than tissue-removing element. This increased flexibility of the flexible distal tip 16 facilitates, for example, centering the tissue-removing element 14 in a desired lesion that is to be removed within the body lumen L to effectively deliver of the catheter 10 into the lesion. As best shown in FIGS. 2 and 3, the distal tip 16 has a proximal end portion coupled to (e.g., directly coupled to) the tissue-removing element 14 and a distal end portion spaced distally from the tissue-removing element. Further, the distal tip 16 defines a tip opening that extends along a length of the distal tip and through the proximal and distal end portions of the distal tip, as best shown in FIG. 3.

As best shown in FIGS. 2 and 3, the flexible distal tip 16 includes a coil 28. The coil 28 is configured to be more flexible than the tissue-removing element 14 and have variable stiffness during a tissue-removing procedure due to the coil tightening and compressing during rotation with the tissue-removing element 14. Further, the coil 28 provides a tapered transition from a guidewire 30 to the tissue-removing element 14, as shown in FIG. 2. The purposes of the increased flexibility of the flexible distal tip 16 in comparison with the tissue-removing element 14 and the tapered transition is to mitigate risk of lesion hang ups and guidewire damage when the catheter 10 is guided through the body lumen L. In one or more embodiments, a diamond grit or other abrasive material can be applied to an exterior surface of the coil 28, preferably on a portion of the coil that may contact the lesion. It is believed the diamond grit or other abrasive material on the coil 28 will aid in loosening a portion of the lesion to center the tissue-removing element in the lesion. Alternatively, the exterior surface of the coil 28, in particular the portion that may contact the lesion or other tissue to be removed, may be surface etched to form an abrasive surface on the coil. As shown, in one or more embodiments the flexible distal tip 16 can further include an annular distal cap 32 secured to the distal end portion of the coil 28. The distal cap 32 may be atraumatic to inhibit injuring the body lumen with the coil 28. The distal cap 32 may also aid in inhibiting unwinding of the coil 28 within the body lumen while still allowing the guidewire 30 to pass through the tip opening. The distal cap 32 may include relatively soft polymeric material that is applied to the distal end portion of the coil and covers the distalmost end of the coil. The polymeric material may adhere turns of the coil to one another. In other embodiments, the distal cap 32 may be replaced by other means for preventing unwinding of the coil 28, such as welding or crimping the coil.

Figure 4:
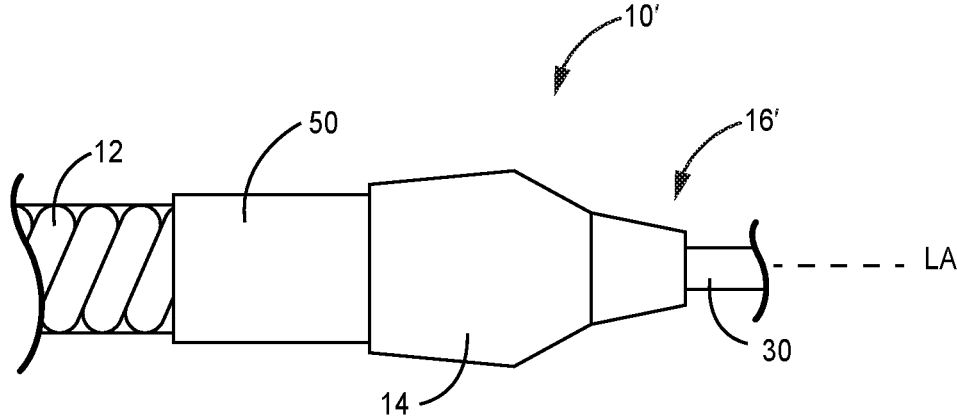
FIG. 4 is an enlarged elevation of an alternative embodiment of the distal end portion of the catheter.
Figure 5:
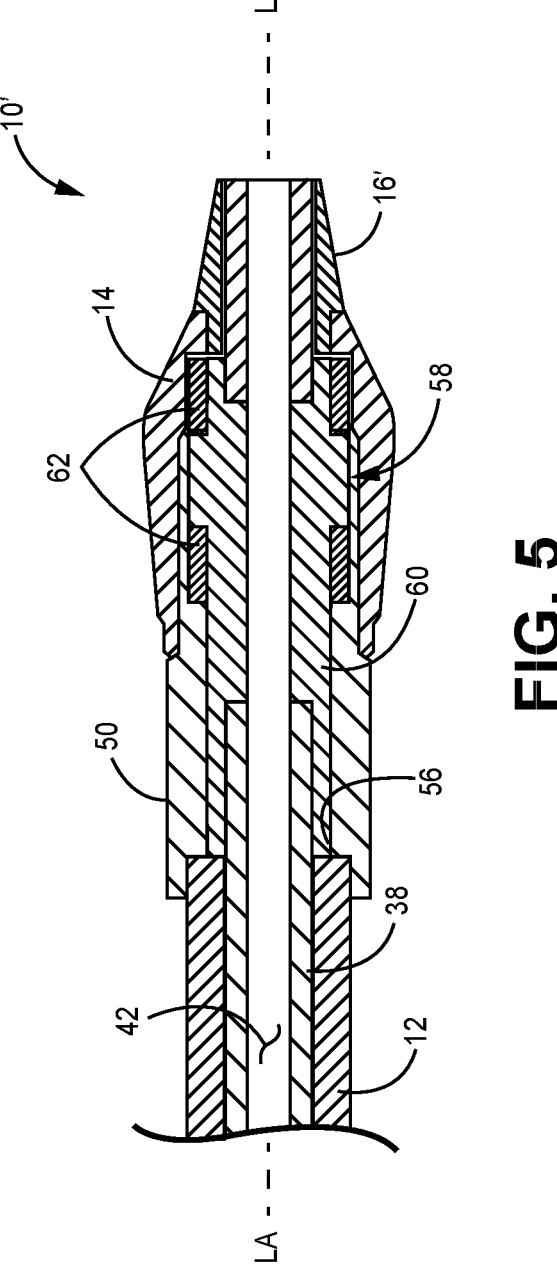
FIG. 5 is an enlarged fragmentary longitudinal cross section of the distal end portion of the catheter in FIG. 4.
Figure 6:
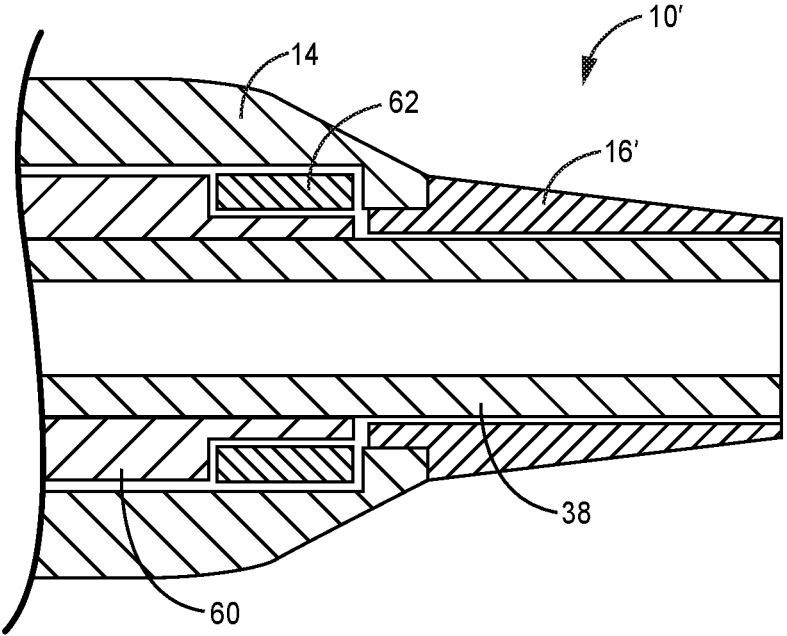
FIG. 6 is an enlarged fragmentary alternative embodiment of a longitudinal cross section of the distal end portion of the catheter in FIG. 4.

Referring to FIGS. 4-6, another embodiment of a catheter 10' includes a different embodiment of a flexible distal tip, generally indicated at reference numeral 16'. The other components of the catheter 10' may be identical to the first embodiment other than the distal tip 16', and therefore, the same components of the catheters 10, 10' are indicated by the same reference numerals in both embodiments. In the present embodiment, the distal tip 16' includes (e.g., may be formed from) a polymeric material. For example, but not limiting to, the polymeric material may be a biocompatible material such as polyethylene or polyetheretherketone, Generally, the polymeric material may have at least some amorphous material, relatively high molecular weight, include backbone chemistry that allows energy to be stored elastically, or include plasticizers as known in the art, which provide a more flexible material than the tissue-removing element 14. The polymeric material forms the distal tip as an integrally formed, one-piece component having an external surface and a wall thickness. In one embodiment, as shown best in FIG. 6, the wall thickness of the distal tip 16' may be non-uniform to promote flexing of the distal tip. Change in wall thickness defines an outer diameter of the distal tip 16' which tapers distally toward its distalmost end. The tapering segments of polymeric material provides a tapered transition from the guidewire 30 to the tissue-removing element 14, best shown in FIG. 4. The increased flexibility of the flexible distal tip 16' in comparison with the tissue-removing element 14 and the tapered transition mitigates risk of lesion hang ups and guidewire damage when the catheter 10' is guided through the body lumen. In one or more embodiments, diamond grit or other abrasive material may be applied to an exterior surface of the polymeric distal tip 16', such as on portions of the distal tip that may contact the lesion or other tissue to be removed. The diamond grit of the distal tip 16 can similarity aid in loosening a portion of the lesion to center the tissue-removing element in the lesion. Alternatively, surface etching on the exterior surface of the distal tip 16', in particular the portion that may contact the lesion or other tissue to be removed, may be surface etched to form an abrasive surface on the distal tip.

In accordance with the present disclosure, the flexible distal tip 16, 16' is atraumatic, such that it is designed and constructed to inhibit damaging (e.g. perforating, dissecting, scraping, cutting, etc.) the body lumen L (e.g., vessel) during delivery of the catheter 10 to the lesion. With reference to the distal tip 16 including the coil 28, the geometry of the coil may be rounded and free from sharp edges that may injure the body lumen. As previously described, the distalmost end of the distal tip 16 may include the atraumatic cap to further mitigate risk of damaging the body lumen L. Turning to the polymeric distal tip 16', its geometry includes the tapering segments such that it is also free from sharp edges that may injure the body lumen L. Moreover, the polymeric material itself may be relatively soft to inhibit puncturing of the body lumen L.

As shown best in FIGS. 3, 5 and 6, in one or more embodiments the catheter 10, 10' including the flexible distal tip 16, 16' coupled to the tissue-removing element 14 may include an inner liner 38. In one embodiment, the inner liner 38 extends axially within the elongate drive member 12, the tissue-removing-element 14, and the distal tip 16. A distalmost end of the inner liner 38 may terminate at the distalmost end of the distal tip 16, 16', as best shown in FIG. 6, or proximal to the distalmost end of the distal tip, as best shown in FIGS. 3 and 5. In another embodiment, the inner liner 38 may extend axially within the elongate drive member 12, the tissue-removing-element 14, but terminate before the distal tip 16, 16' such that the inner liner is not received in the distal tip, as shown in FIGS. 3 and 5. The inner liner 38 is a low friction material to reduce friction imparted on the guidewire 30 when the guidewire is received in the inner liner. An inner layer of the inner liner 38 may include a polymeric material, such as polytetrafluoroethylene, perfluoroalkoxy, fluorinated ethylene propylene, and/or combination thereof as the low friction material. In other embodiments, the catheter 10, 10' may not include the inner liner 38.

Figure 7:
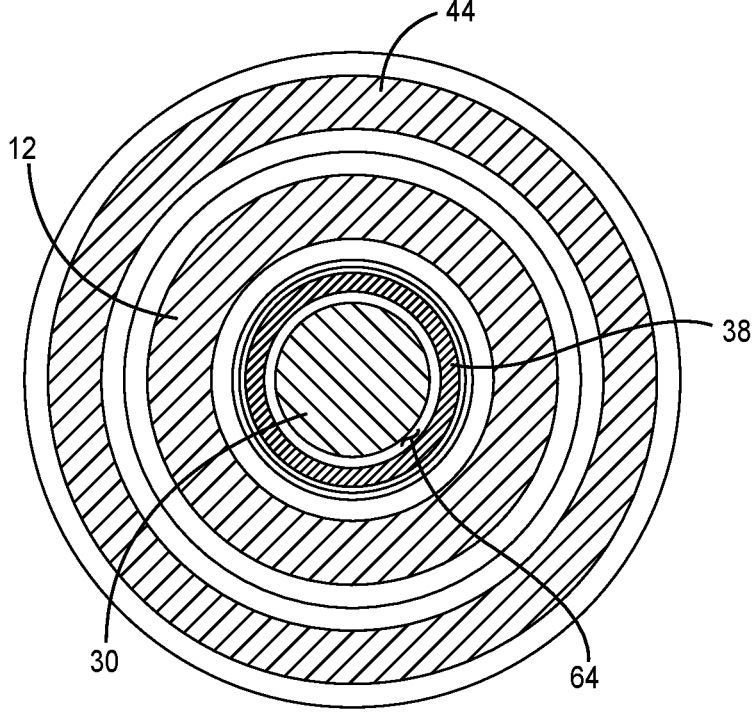
FIG. 7 is a cross section taken through line 3-3 in FIG. 2.

As best shown in FIG. 4, the elongate drive member 12 in the illustrated embodiment comprises a drive coil. The elongate drive member 12 may be another drive member other than the drive coil, such as a drive shaft, a drive lumen, or other type of elongate drive member. As best shown in FIGS. 3, 5, and 7, the elongate drive member 12 in the illustrated embodiment is disposed around the inner liner 38 to define a liner passage 42. The elongate drive member 12 and inner liner 38 extend along the longitudinal axis LA of the catheter 10 from the proximal end portion 18 to the distal end portion 20, as best shown in FIGS. 1 and 3. An isolation sheath 44 is disposed around the drive coil of the elongate drive member 12, as shown in FIGS. 1, 2, 7, and 8. The drive coil and the inner liner 38 are both configured to translate relative to the isolation sheath 44. The isolation sheath 44 isolates the body lumen L from at least a portion of the drive coil and inner liner 38.

As shown in FIG. 2, the tissue-removing element 14 engages and removes tissue T in the body lumen L when centered in the lesion. Any suitable tissue-removing element 14 for removing tissue T in the body lumen L as it is rotated may be used in one or more embodiments. In the illustrated embodiment, the tissue-removing element 14 comprises an abrasive burr configured to abrade tissue in the body lumen L when a motor 48, as best shown in FIG. 1, rotates the abrasive burr. The abrasive burr has an abrasive outer surface formed, for example, by a diamond grit coating, surface etching, or the like. In other embodiments, the tissue-removing element can comprise one or more cutting elements having smooth or serrated cutting edges, a macerator, a thrombectomy wire, etc. In the illustrated embodiment, as best shown in FIGS. 3, 4, and 5, a coupler 50 couples the tissue-removing element 14 to a distal end portion of a drive member, such as the elongate drive member 12. The coupler 50 transfers rotation from the drive member to the tissue-removing element 14. Together, the coupler 50 and the tissue-removing element 14 define an internal cavity 56 extending axially along the longitudinal axis LA. The coupler 50 may be formed from metal or other material, and may be welded and/or crimped to the drive coil and the tissue-removing element 14. The coupler 50 may be fixedly coupled to the drive coil 12 and the tissue-removing element 14 in other ways. In one or more embodiments, the catheter 10, 10' may not include the coupler, but instead, the drive coil 12 may be fixedly coupled directly to the tissue-removing element 14, such as by welding or in other ways.

The illustrated catheter 10, 10', best shown in FIGS. 3 and 5, also includes an internal bearing assembly, generally indicated at 58, received in the tissue-removing element 14 and the coupler 50. The internal bearing assembly 58 is configured to facilitate rotation of the tissue-removing element 14 without damaging the inner liner 38. The internal bearing assembly 58 may include a bushing 60 through which the inner liner 38 extends, and one or more bearings 62 coupled to the tissue-removing element 14 and/or the coupler 50 to facilitate rotation about the bushing.

Figure 8:
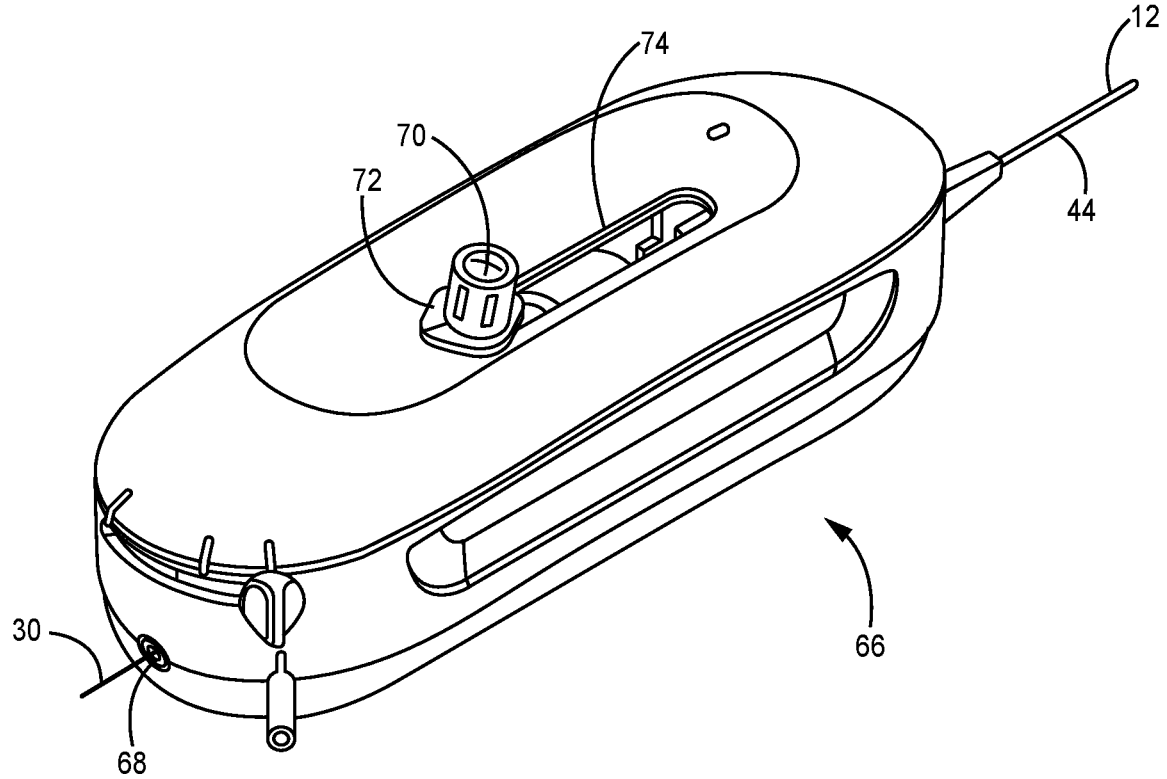
FIG. 8 is a perspective of a handle of the catheter.

To remove tissue T in the body lumen L of a subject, a practitioner inserts the guidewire 30 into the body lumen of the subject, to a location distal of the tissue that is to be removed, as best shown in FIG. 2. Subsequently, the practitioner inserts the proximal end portion of the guidewire 30 through a guidewire lumen 64 of the inner liner 38 and through a handle 66 so that the guidewire extends through a proximal port 68 in the handle, as best shown in FIGS. 1, 7, and 8. With the catheter 10, 10' loaded onto the guidewire 30, the practitioner advances the catheter along the guidewire until the tissue-removing element 14 is positioned proximal and adjacent the tissue, as best shown in FIG. 2. When the tissue-removing element 14 is positioned proximal and adjacent the tissue, the practitioner actuates the motor 48 using an actuator 70 to rotate the drive coil 12 and the tissue-removing element. The tissue-removing element 14 abrades (or otherwise removes) the tissue T in the body lumen L as it rotates. While the tissue-removing element 14 is rotating, the practitioner may selectively move the drive coil and inner liner 38 distally along the guidewire 30 to abrade the tissue and, for example, increase the size of the passage through the body lumen L. The practitioner may also move the drive coil 12 and inner liner 38 proximally along the guidewire 30, and may repetitively move the components in distal and proximal directions to obtain a back-and-forth motion of the tissue-removing element 14 across the tissue by sliding an advancer 72 back and forth within a slot 74 in the handle 66, as best shown in FIGS. 1 and 8. During the abrading process, the inner liner 38 isolates the guidewire 30 from the rotating drive coil 12 and tissue-removing element 14 to protect the guidewire from being damaged by the rotating components. As such, the inner liner 38 is configured to withstand the torsional and frictional effects of the rotating drive coil and tissue-removing element 14 without transferring those effects to the guidewire 30. When the practitioner is finished using the catheter 10, 10', the catheter can be withdrawn from the body lumen L and unloaded from the guidewire 30 by sliding the catheter proximally along the guidewire. The guidewire 30 used for the abrading process may remain in the body lumen L for use in a subsequent procedure.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:
    an elongate drive member having an axis and proximal and distal end portions spaced apart from one another along the axis, the elongate drive member being sized and shaped to be received in the body lumen and configured to be rotated about the axis;
    a tissue-removing element operatively coupled to the distal end portion of the elongate drive member, the tissue-removing element being configured to be rotated by the elongate drive member to remove the tissue in the body lumen; and
    a distal tip extending distally outward from the tissue-removing element and being configured to be more flexible than the tissue-removing element, wherein the distal tip has a proximal end portion coupled to the tissue-removing element and a distal end portion spaced distally from the tissue-removing element, the distal tip defining a tip opening extending through the proximal and distal end portions,
    wherein the distal tip comprises a coil,
    wherein the coil is configured to increase stiffness of the distal tip by compressing during rotation with the tissue-removing element.

2. The tissue-removing catheter as set forth in claim 1, wherein the distal tip further comprises a cap secured to the coil.

3. The tissue-removing catheter as set forth in claim 2, wherein the cap is secured directly to the coil at a distal end portion of the coil to inhibit unwinding of the coil.

4. The tissue-removing catheter as set forth in claim 3, wherein the cap covers a distalmost end of the coil.

5. The tissue-removing catheter as set forth in claim 4, wherein the cap comprises a polymeric material and is atraumatic.

6. The tissue-removing catheter as set forth in claim 3, wherein the cap adheres turns of the coil to one another.

7. The tissue-removing catheter as set forth in claim 1, wherein the coil has an abrasive exterior surface.

8. The tissue-removing catheter as set forth in claim 1, further comprising an inner liner disposed in the tip opening, wherein the inner liner is configured to receive a guidewire.

9. The tissue-removing catheter as set forth in claim 8, wherein the inner liner includes a low friction material to reduce friction imparted on the guidewire when the guidewire is received in the inner liner.

10. The tissue-removing catheter as set forth in claim 8, wherein the inner liner extends proximally into the drive shaft.

11. The tissue-removing catheter as set forth in claim 8, wherein a distalmost end of the inner liner does not extend distally beyond a distalmost end of the distal tip.

12. The tissue-removing catheter as set forth in claim 1, wherein the elongate drive member comprises a drive coil.

13. A tissue-removing catheter for removing tissue in a body lumen, the tissue-removing catheter comprising:

an elongate drive member having an axis and proximal and distal end portions spaced apart from one another along the axis, the elongate drive member being sized and shaped to be received in the body lumen and configured to be rotated about the axis;

a tissue-removing element operatively coupled to the distal end portion of the elongate drive member, the tissue-removing element being configured to be rotated by the elongate drive member to remove the tissue in the body lumen; and a distal tip extending distally outward from the tissue-removing element and being configured to be more flexible than the tissue-removing element, wherein the distal tip has a proximal end portion coupled to the tissue-removing element and a distal end portion spaced distally from the tissue-removing element, the distal tip defining a tip opening extending through the proximal and distal end portions, wherein the distal tip comprises a polymeric material, wherein the distal tip has a tapering portion defining a wall thickness that tapers toward the distal end portion of the distal tip to promote flexing of the distal tip.

14. The tissue-removing catheter as set forth in claim 13, further comprising an inner liner disposed in the tip opening of the distal tip, wherein the inner liner is configured to receive a guidewire.

15. The tissue-removing catheter as set forth in claim 14, wherein the inner liner includes a low friction material to reduce friction imparted on the guidewire when the guidewire is received in the inner liner.

16. The tissue-removing catheter as set forth in claim 14, wherein the inner liner extends proximally into the drive shaft.

17. The tissue-removing catheter as set forth in claim 14, wherein a distalmost end of the inner liner does not extend distally beyond a distalmost end of the distal tip.

\* \* \* \* \*